United States Patent [19]

Cirulis et al.

[11] 3,973,430
[45] Aug. 10, 1976

[54] WATER POLLUTION MONITOR

[75] Inventors: Uldis Cirulis, Midland Park; Ellis M. Zacharias, Jr., Ridgewood, both of N.J.

[73] Assignee: Process and Pollution Controls Company, Tulsa, Okla.

[22] Filed: Mar. 11, 1975

[21] Appl. No.: 557,393

Related U.S. Application Data

[63] Continuation-in-part of Ser. No. 383,405, July 27, 1973, Pat. No. 3,892,127.

[52] U.S. Cl. .............................. 73/61.1 R; 73/560
[51] Int. Cl.² ...................................... G01N 29/02
[58] Field of Search ............... 73/61.1 R, 61 R, 53, 73/67.5 R, 67.6, 24, 1 R, 560; 324/61 R, 65 R; 356/70; 23/230 HC, 230 R

[56] References Cited
UNITED STATES PATENTS

| | | | |
|---|---|---|---|
| 3,359,788 | 12/1967 | Colvin | 73/61.1 R |
| 3,710,615 | 1/1973 | Johnson et al. | 73/61 R |
| 3,789,655 | 2/1974 | Passeri | 73/24 |
| 3,791,200 | 2/1974 | Hayre | 73/61 R X |
| 3,892,127 | 7/1975 | Cirulis et al. | 73/61.1 R |

FOREIGN PATENTS OR APPLICATIONS

784,146 10/1957 United Kingdom.............. 73/24

OTHER PUBLICATIONS

Zacharias, E. M., Process Measurements by Sound Velocimetry, in Instr. and Control Systems, pp. 112-113, Sept. 1970.

*Primary Examiner*—Richard C. Queisser
*Assistant Examiner*—Joseph W. Roskos
*Attorney, Agent, or Firm*—Samuelson & Jacob

[57] ABSTRACT

A system for detecting the concentration of hydrocarbons (petroleum products) or other pollutants in water having a differential sound velocimeter which compares the velocity of sound in the liquid under study with the velocity of sound in the liquid (largely water) from which the oil or other pollutant has been separated by mechanical and/or solvent extraction means. A suitably calibrated frequency-to-analog converter is utilized to indicate the amount of the oil concentration and/or shutdown the water transporting system if the concentration exceeds a predetermined value.

60 Claims, 13 Drawing Figures

WATER POLLUTION MONITOR

This application is a continuation-in-part of application Ser. No. 383,405, filed July 27, 1973, now U.S. Pat. No. 3,892,127.

The invention relates to a system and a method of determining the concentration of oil, other petroleum products or hydrocarbons, generally, in water. More particularly, the invention achieves its greatest use in the measurement of the concentration of oil contained in the ballast liquid carried by tankers and in the measurement of the concentration of petroleum products in the effluent from refineries.

Tankers take on sea water after they have delivered the oil or other petroleum products carried in their tanks at the port of delivery. In order to enable the vessel to ride well in the water while it is returning from the port of delivery to the port at which it picks up its products, the vessel fills its tanks with a ballast of sea water at the port of oil delivery. This sea water may contain a large quantity of impurities and, in addition, the tank may not have been completely purged of the cargo. Consequently, the water may well contain a quantity of petroleum or other contaminants.

While en route to and upon arrival at the port at which the tanker is to take on its cargo of oil and/or other petroleum products, the vessel purges its cargo tanks of the ballast water. Since it is ecologically unsound to discharge petroleum products above a certain concentration into the open sea and the harbor, it is necessary to measure the concentration of petroleum product in the ballast water prior to and during discharge into the open sea and into the harbor.

Accordingly, it is an important object of the invention to provide a system for detecting the quantity of hydrocarbon such as oil in the water down to perhaps 10 or less ppm (parts per million).

It is a further object of the invention to provide such a system whereby the measurement is carried on by a differential sound velocimeter having two sound paths (one for the standard, the other for the tank discharge) which paths are as close to being identical as is possible.

It is yet another object of the invention to provide such a system wherein the standard and the sample are kept at or near the ideal temperature for making sound velocity measurements.

It is a still further object of the invention to provide such a system which may be used for various types of petroleum products having different sound propagation characteristics.

These and other objects, advantages, features and uses will be apparent during the course of the following description.

Broadly, the invention comprises a system for comparing the sound velocity characteristics of the contents of the tank being discharged with the sound velocity characteristics of the water being discharged from the same tank. This is accomplished by dividing a portion of the flow from the tank into a standard and an unknown. The standard is obtained by removing the suspended and undissolved solids and hydrocarbons (petroleum products) from the water by mechanical means such as a coalescing filter type oil separator, with or without supplementary solvent extraction. This leaves the water principally containing dissolved components as the standard.

Both the standard and the unknown sample are run through a common high temperature bath so that they are both at the same temperature, near the point at which the slope of the sound velocity temperature curve is close to zero. This occurs in sea water with 3.5% dissolved salt at about 72°C. The sound velocity in the standard is measured by a sound velocimeter, preferably using a single transducer and a reflector having an acoustic impedance different from that of the water to obtain good reflection. The transducer acts as both a transmitter and receiver.

The sound velocity in the sample is measured by a sound velocimeter which is as identical as possible to the velocimeter measuring the sound velocity in the standard. Every effort should be made to keep the path lengths identical and to use transducers which are matched as closely as possible. It is also important that the elements of the sound velocimeter have the same coefficient of thermal expansion. A single transmitter-receiver electronic system is utilized to excite the transducers and to receive the signals from them on a time shared basis. Use of a single electronics system eliminates any common mode errors such as relative drift which might arise if two independent electronic systems were used.

The received signals are compared to obtain a difference frequency. The difference frequency is converted to an analog voltage which is proportional to the difference in the sound velocities and thus to the concentration of the hydrocarbons in the water. The output analog voltage may be used for visual display and/or to actuate an alarm or to shut the system down. The analog voltage may also be used to feed a chart recorder or it may be converted to a digital output for control or other purposes. It is frequently advisable to include a temperature compensation circuit and to include a temperature correction signal in the system. This makes it possible to obtain accurate measurement of the amount of petroleum product pollution which is free of temperature dependence.

In the drawing, wherein like numerals are used to designate like parts throughout the same.

In the drawing, wherein, for the purpose of illustration, there are shown embodiments of the invention and wherein like numerals designate like parts throughout the same, the numeral 20 designates a system of the invention generally. System 20 (FIG. 1) is seen to comprise a plurality of input valves $22^1$, $22^{22}$ . . . $22^n$ for selecting the output from any one of the tanks for measurement while the tank contents are being discharged, a valve 24 connected to a source of cleansing and flushing solution for cleaning the measuring system, a separator 26 such as a coalescing type filter or a De Laval centrifugal separator and a differential transducer assembly 28.

Figure 1:
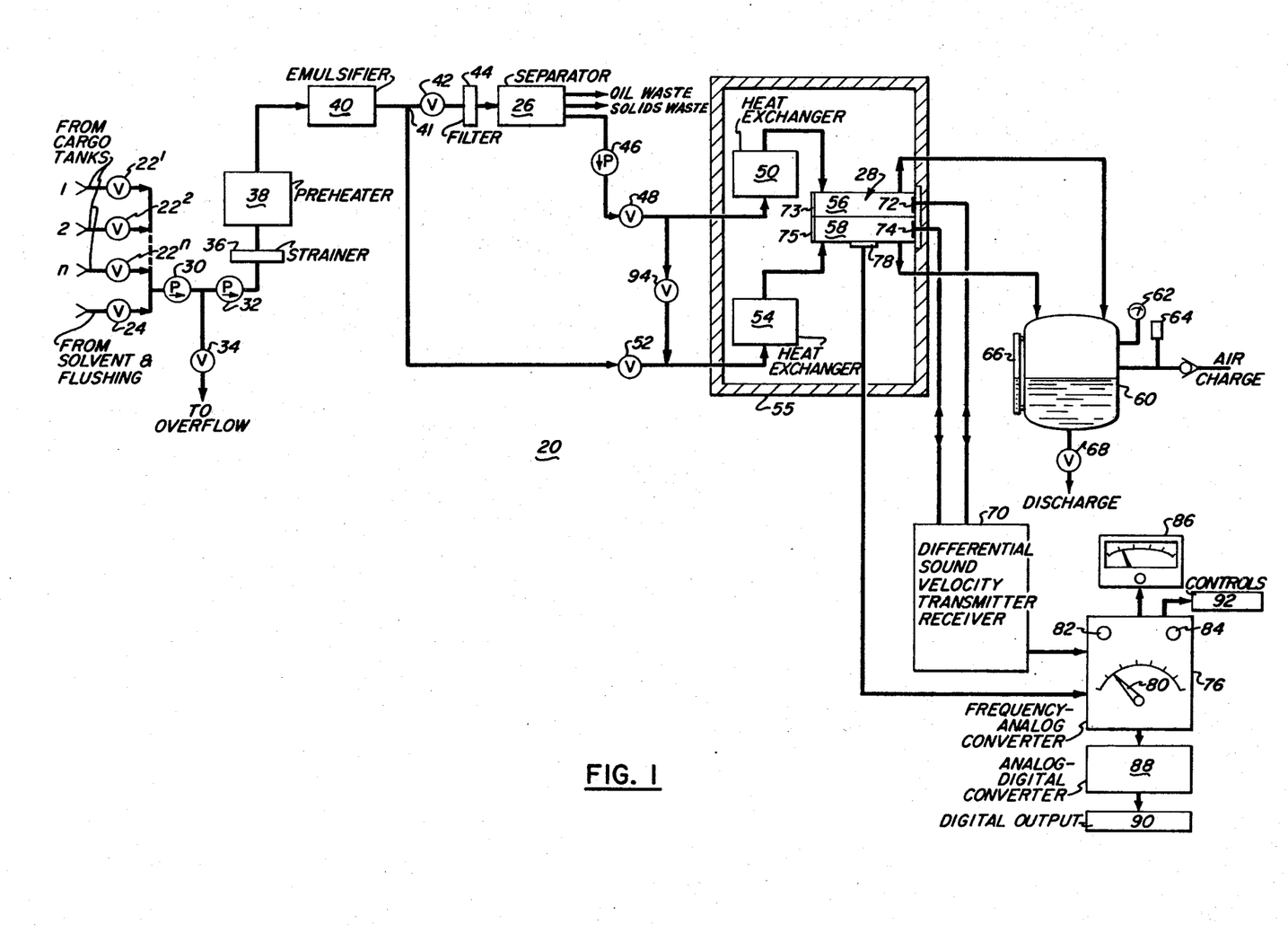
FIG. 1 is a block diagram of an embodiment of a system of the invention.

Upon opening one of the valves 22, pumps 30 and 32 are turned on. Since a small amount of the sample solution is needed to operate the measuring system, valve 34 is opened, as desired, to deliver the excess, overflow liquid to the source tank or to a storage tank.

A sample solution from one of the tanks, as selected by the appropriate valve 22 is pumped on a substantially continuous flow basis by pumps 30 and 32 to a strainer 36 which stops the large debris but does not preclude the passage of oil therethrough. Under certain conditions (solution without large solids), the strainer 36 may be omitted from the system. The flow of the sample solution next reaches an optional preheater 38 which should be used to raise the solution temperature to about 50° to 65°C. If the solution temperature is already in that range, the preheater is unnecessary. The solution reaches an optional emulsifier 40 next. The emulsifier 40 is utilized to break the large hydrocarbon droplets into small ones so that the hydrocarbons are more uniformly distributed through the solution. Emulsification is also obtained, in some degree, from the operation of the liquid transporting pumps.

At a junction 41, some of the solution flows to a valve 42 which, when open, feeds a portion of the solution to a filter 44 and the separator 26. The filter 44 is preferably of very fine mesh in order to remove the fine solids from the solution. The separator 26, which is preferably a coalescing type filter or a De Laval centrifugal separator, removes the oil and solids from the water and leaves a standard solution of water to be pumped by a pump 46 through a control valve 48 to a heater exchanger 50. The other portion of the solution (unknown) flows through a valve 52 to a heat exchanger 54. Both heat exchangers and differential transducer assembly 28 are mounted in an insulated tank 55 containing a constant temperature bath for holding the temperature of the standard and unknown at the same temperature, preferably 72° ± 1°C for reasons which will be evident as this description proceeds. The heat exchangers may also be mounted outside the constant temperature bath. In such cases, the liquid from the constant temperature bath may be circulated through the heat exchangers. In any event, it is important that the temperatures of the two solutions in the differential transducer be equal within ± 0.1°C.

The standard solution enters transducer assembly (velocimeter) 56 and the unknown solution enters transducer assembly (velocimeter) 58. Both solutions are kept under pressure because the outputs of both assemblies 56 and 58 are fed to a tank 60 which is kept under pressure by an air charge and which serves to keep the pressures in assemblies 56 and 58 equal. The usual pressure gauge 62 and pressure relief valve 64 are provided. When the liquid in tank 60 reaches a predetermined level, valve 68 is opened by a liquid level control mechanism (not shown) to discharge some of the liquid from tank 60. A sight glass 66 is used for visual monitoring of the liquid level in tank 60.

As the solutions flow through transducer assemblies 56 and 58, a differential sound velocity transmitter-receiver alternately applies a pulse to transducer 72 and to transducer 74. The pulse excites the transducer 72 which transmits an acoustic wave to reflector 73. The wave is returned to transducer 72 and the electrical signal produced is fed to differential sound velocity transmitter-receiver 70. Similarly, the pulse excites transducer 74 and the acoustic wave produced is reflected back to transducer 74 by reflector 75. The shift between excitation of transducer 72 and transducer 74 cannot be more rapid than the travel time of the acoustic waves.

The output of differential sound velocity transmitter-receiver 70 is a frequency difference which is applied to a frequency to analog converter 76. A temperature sensor 78 in combination with a signal from sound velocity transmitter-receiver 70 will cause a ready light 82 to illuminate when the temperature of the bath is 72°C ± 1°C and the differential sound velocity transmitter-receiver 70 is in phase lock condition. Frequency to analog converter 76 may be provided with a control 80 which is positioned depending upon the type of hydrocarbon in the tank solution. It adjusts the sensitivity of the converter 76. Indicator light 84 illuminates when the oil concentration is above a predetermined value.

The output of converter 76 may be fed to an analog display 86 and/or to an analog to digital converter 88 and then to a digital output 90. One or more controls 92 to shut down the system and/or actuate an alarm may be connected to converter 76.

In order to calibrate the system, valve 52 should be closed and a valve 94 is opened. Thus, a standard solution flows through both transducer assemblies making it possible to adjust the system in the manner which will be described further on in this specification.

Figure 2:
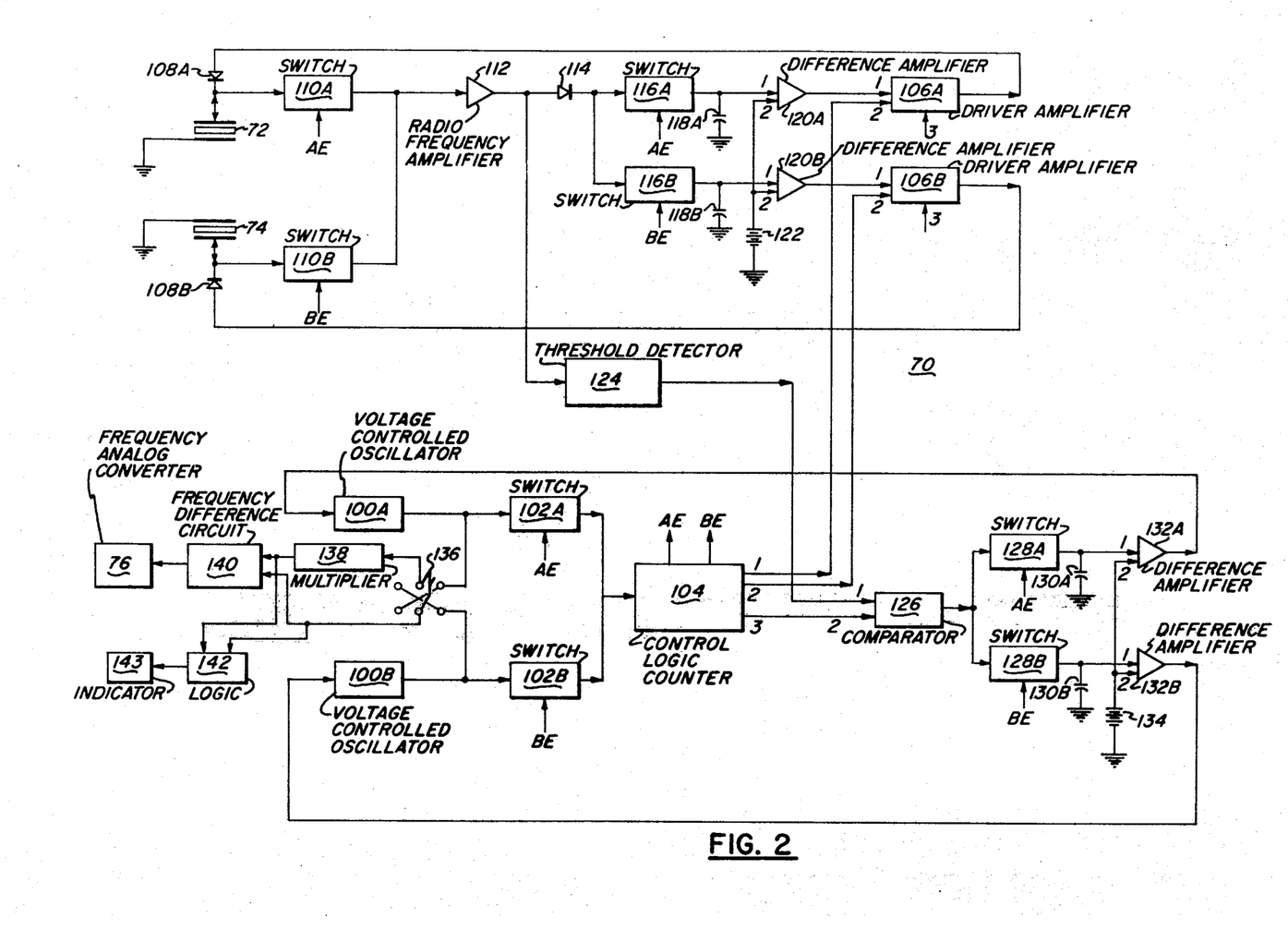
FIG. 2 is a block diagram of the transmitter-receiver used in the system of FIG. 1.

FIG. 2 is a block diagram of differential sound velocity transmitter-receiver 70. The designation AE is used to signify the enabling of the circuits associated with transducer 72 and the designation BE is used to signify the enabling of the circuits associated with transducer 74.

Considering the circuit of FIG. 2, and assuming that the AE circuits are on so that transducer 72 has excitation applied to it from voltage controlled oscillator 100A through switch 102A, control logic counter 104 to input 2 of driver amplifier 106A and decoupling means 108A which is preferably a diode. Switch 102A is preferably a logic gate which is "on" when AE is "on" and is "off" where there is no AE signal present.

The excitation signal is changed by transducer 72 to an acoustic wave which is transmitted to reflector 73 and back to transducer 72. Now, transducer 72 converts the acoustic wave into an electrical signal which is blocked by diode 108A so that the signal goes through switch 110A, which is preferably a field effect transistor which is "on" when AE is "on" and is "off" when there is no AE signal present. The signal then is applied to the input of radio frequency amplifier 112. The output of radio frequency amplifier 112 is connected to peak detector diode 114 which is, in turn, connected to switch 116A. Switch 116A is similar to switch 110A.

The output of switch 116A is connected to capacitor 118A and to input 1 of difference amplifier 120A. The charge on capacitor 118A is proportional to the amplitude of the received pulse received by transducer 72 and serves to vary and control the amplitude of the excitation pulse. This is accomplished by comparing the voltage on input 1 of difference amplifier 120A with the reference voltage applied to input 2 from source 122.

The output of difference amplifier 120A is applied to input 1 of driver amplifier 106A and serves to raise or lower the output excitation signal, as required. Input 3 of driver amplifier 106A is used to obtain adjustable delay.

Input 3 is used to provide a manual adjustment to equalize the delays in the A and B channels. The delay adjustment consists of adjusting a small trimmer capacitor. The delay introduced is a function of the size of this trimmer capacitor.

The loop just described can be designated an electronic amplitude servo circuit since it serves to control the amplitude of the excitation signal applied to the transducer. Thus, it can be seen that the amplitude may be changed to accommodate changes in the acoustic attenuation in the path which is encountered, for example, with a slight change in the solution in the housing.

The output of radio frequency amplifier 112 is also connected to the input of a threshold detector 124 which passes signals above a certain predetermined value to input 1 of comparator 126. A signal from output 3 of control logic counter 104 is applied to input 2 of comparator 126. The signal output of comparator 126 flows through switch 128A, which is similar to switches 110A and 116A, to input 1 of difference amplifier 132A and to capacitor 130A. The charge on capacitor 130A is proportional to the pulse repetition frequency.

Control logic counter 104 turns off AE and turns on BE so that transducer 74 now transmits an acoustic wave to reflector 75 which reflects the wave back to transducer 74. The operation just described for condition AE now takes place for condition BE utilizing all the elements designated with the suffix B and those elements which are common to both systems A and B. The critical components are common to both modes so that there is a minimum of error due to the mismatching of these components which would probably occur if two such elements were used (one in each system). The common components are radio frequency amplifier 112, peak detector diode 114, threshold detector 124, control logic counter 104 and comparator 126.

The outputs of voltage controlled oscillators 100A and 100B are fed through a switch 136 positioned so that the oscillator having the higher frequency is fed to a multiplier 138, which may be more generally described as a zeroing device, and then to a frequency difference circuit 140. The output of the other oscillator is fed directly to frequency difference circuit 140. The output of frequency difference circuit 140 is fed to frequency-to-analog converter 76. Discussion of the positioning of switch 136, which is part of the calibration procedure, will be covered later in this description. The inputs of a logic 142 are connected in shunt with the inputs of frequency difference circuit 140. Logic 142 is utilized to activate an indicator 143.

By way of example, the following illustration assumes that the frequency of oscillator 100B is higher and its output is connected to multiplier 138 through switch 136. The output of oscillator 100A is fed directly to frequency difference circuit 140.

Figure 3:
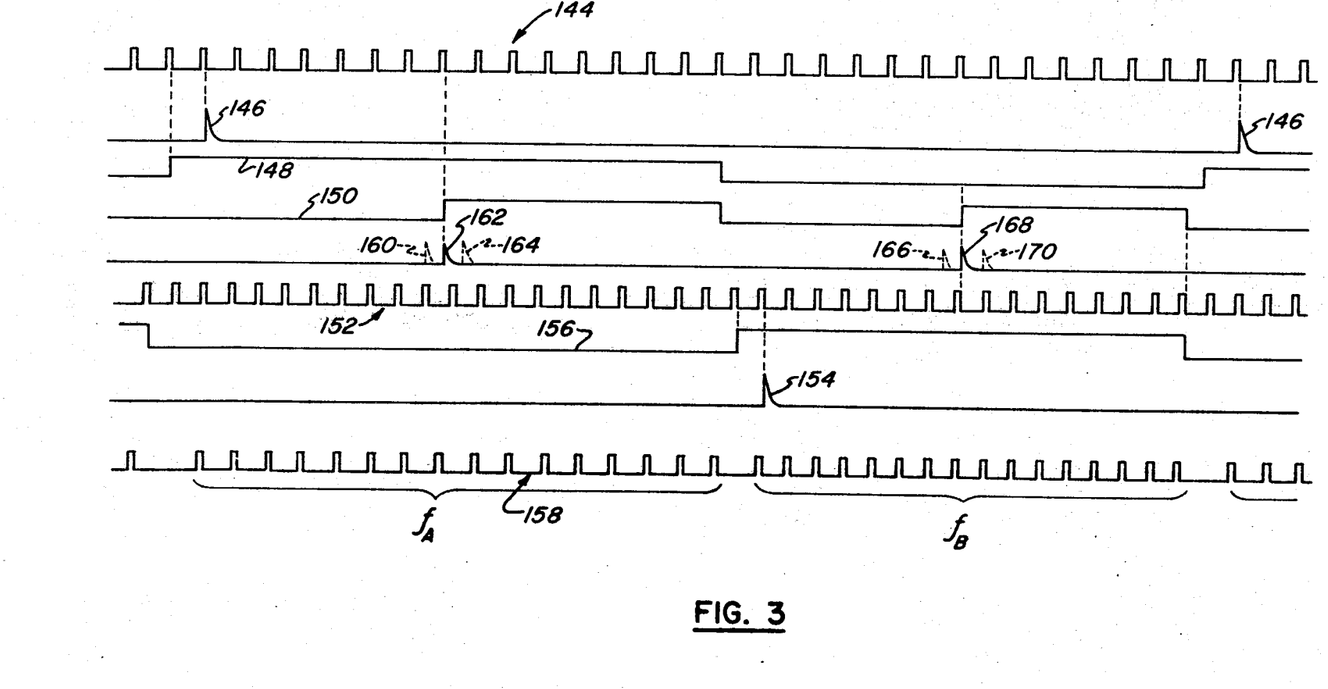
FIG. 3 is a timing diagram of the system of FIG. 2.

The operation of the differential sound velocity system of the invention will best be understood by an examination of FIG. 3. Curve 144 represents the pulse train which is transmitted by voltage controlled oscillator 100A. Pulses 146 are the pulses which are applied to transducer 72 to produce an acoustic pulse which is transmitted toward the reflector 73 and back to transducer 72.

Curve 148 represents the AE "on" condition when positive and the "off" condition when zero. Curve 150 is the representation of the comparator reference signal. Curve 152 represents the pulse train which is transmitted by voltage controlled oscillator 100B and pulses 154 are those which are applied to transducer 74 to produce an acoustic pulse which is transmitted to reflector 75 and back to transducer 74.

Curve 156 represents the BE "on" condition when positive and the "off" condition when zero. Curve 158 represents the combined pulse trains from oscillators 100A and 100B, those from oscillator 100A are designated $f_A$ and appear when AE is on and those from oscillator 100B are designated $f_B$ and appear when BE is on.

Pulses 160, 162 and 164 represent the three possible positions at which an acoustic pulse transmitted by transducer 72 may appear at the output of the threshold detector 124. Pulses 166, 168 and 170 represent the three possible positions at which an acoustic pulse transmitted by transducer 74 may appear at the output of the threshold detector 124.

Pulses 162 and 168 have arrived at the correct time, namely at the positive-going edge of the comparator reference curve 150. In these conditions, no frequency corrections are made. Pulses 160 and 166 arrive too early. Under these conditions, the associated oscillator frequency is increased. Pulses 164 and 170 arrive too late and under these conditions, the associated oscillator frequency is decreased.

Operation proceeds as follows:
1. AE on
2. Pulse 146 is applied to transducer 72 and an acoustic pulse is transmitted across the fluid.
3a. Pulse 162 received — no frequency correction. or
3b. Pulse 160 received — frequency of oscillator 100A is increased, or
3c. Pulse 164 received — frequency of oscillator 100A is decreased.
4. At some subsequent time AE is turned off by control logic counter 104.
5. BE on
6. Pulse 154 is applied to transducer 74 and an acoustic pulse is transmitted across the fluid.
7a. Pulse 168 received — no frequency correction. or
7b. Pulse 166 received — frequency of oscillator 100B is increased, or
7c. Pulse 170 received — frequency of oscillator 100B is decreased.
8. The signal represented by curve 158 containing $f_A$ during AE on and $f_B$ during BE on is used as input to the control logic counter 104. The signals represented by curves 144 and 152 ($f_A$ and $f_B$ respectively) are applied to a frequency difference circuit whose output is utilized as described heretofore.

To calibrate the system valve 52 is closed and valve 94 is opened. Thus, the standard solution is fed to both transducer assemblies 56 and 58. Now, the multiplier (zeroing circuit) 138 is adjusted to have a multiplication factor of unity so that the position of switch 136 does not affect the measurements for calibration.

The system is turned on and the output of logic 142 is connected to an indicator 143 which indicates which frequency is higher. Indicator 143 may be a meter, lights, an oscilloscope or any other indicator. Switch 136 is then thrown to the position in which the output of the oscillator having the higher frequency is connected to multiplier 138. Now, multiplier 138, which serves as a zeroing circuit and can only multiply by a factor less than unity, is adjusted so that the frequency outputs of the two oscillators are equal.

To place the system in condition for operation, valve 94 is closed and valve 52 is opened. Now, the standard solution will be measured by transducer assembly 56 and the unknown solution will be measured by transducer assembly 58.

Figure 4:
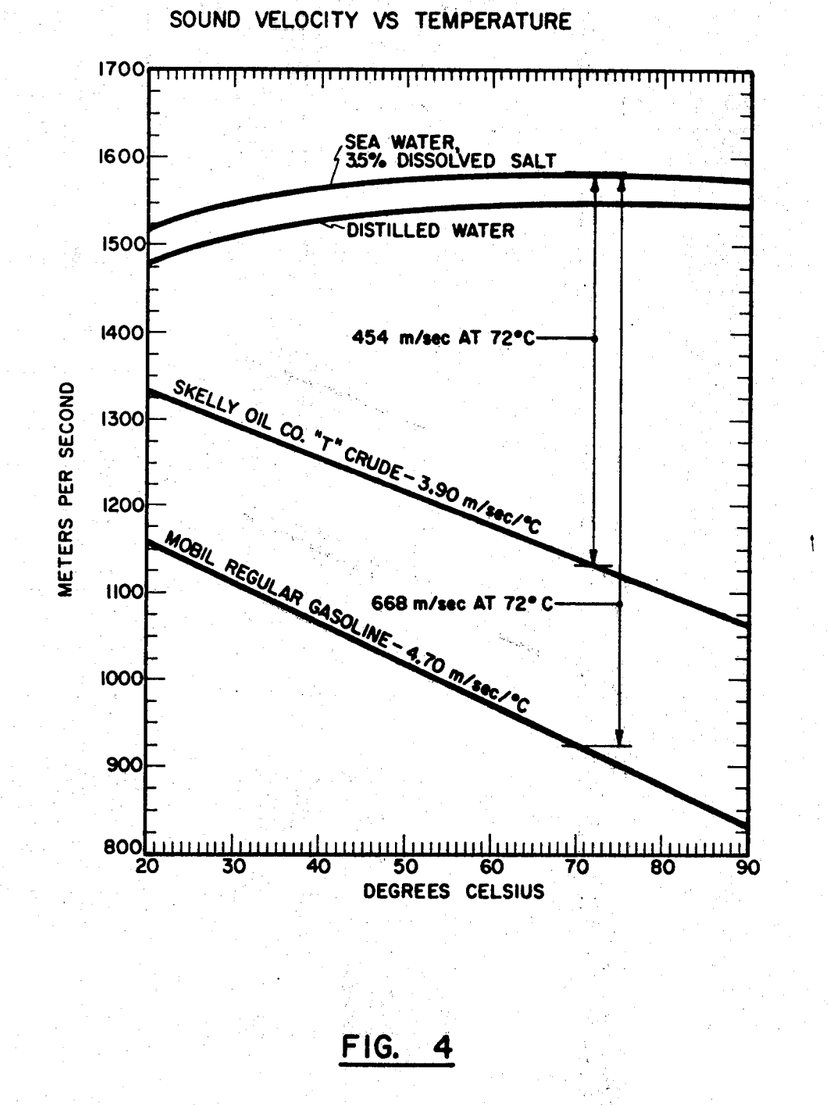
FIG. 4 is a plot of sound velocity against temperature for several different liquids.

FIG. 4, which is a plot of sound velocity against temperature for various liquids, illustrates the desirability of raising the temperature of the solutions to 72°C ± 1° and maintaining the temperature within that range. It is seen that both the 3.5% dissolved salt sea water and distilled water curves are flat in that region so that it is possible to endure slight temperature variation without experiencing a large error in measurement.

The plots of the two hydrocarbons are examples and most hydrocarbons carried by tankers fall into a family of curves having negative slopes of about the order $-3$ to $-5$ $m/s/°C$. Accordingly, it can be seen that accurate measurement will be obtained if the constant temperature bath is kept within the aforementioned range.

System 520 (FIG. 1A) is seen to have an input valve 522 which is connected to the deballasting line from one or more of the ballast tanks. If desired, there may be a plurality of input valves 522 similar to the input valves 22 of FIG. 1. A valve 524 is connected to a source of solvent and cleaning solution and valve 525 is connected to the flushing tank. A valve 527 is connected to the outputs of valves 524 and 525 to permit cross feeding of the cleaning solution and the flushing liquid. Check valves 531 are provided to prevent feed of liquid back through the input valves.

Figure 1A:
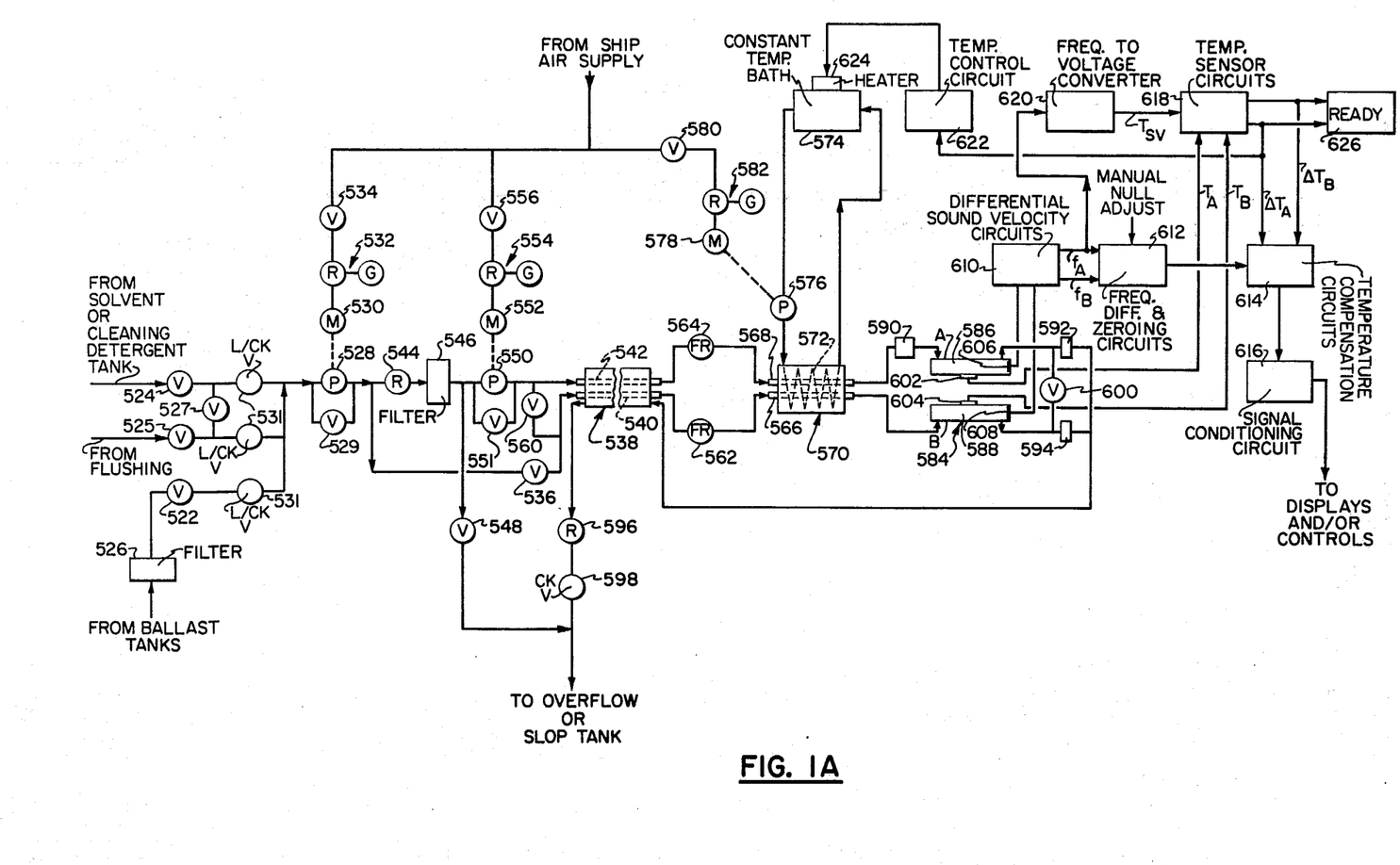
FIG. 1A is a block diagram of a further embodiment of a system of the invention.

When valve 522 is opened, a sample of the deballasting water is brought through a particulate filter 526 to remove large particles which might damage the pumps and other mechanical elements of the system. The sample is fed through a gear pump 528 which normally delivers an output of approximately 1 gallon per minute at a pressure of about 150 psi. Pump 528, when used aboard ship, is preferably by an air motor 530 which receives its power from the ship air supply (about 80 psi) through a valve 534 and a regulator and gauge 532. Clearly, other sources of motive power may be used to drive pump 528. A by-pass control valve 529 is connected across the pump 528.

It can readily be seen that the pump 528 may be connected to the solvent or cleaning detergent tank or to the flushing line which normally contains clean sea water.

The discharge of the pump 528 is divided into two streams. One stream passes through a stop valve 536 into a tube 540 in an economizer heat exchanger 538. The other stream passes through a pressure reducer 544 which reduces the pressure to say, about 20 psi and a filter 546 such as a coalescing filter which removes suspended oil down to about 5 – 10 parts per million (ppm) and allows all dissolved matter, including dissolved oil, to pass through it. Other types of separators such as the De Lavel separator will also work but a coalescing filter is preferable. Most of the liquid flowing through filter 546 is discharged to the main drain or a slop tank through a throttling or back pressure valve 548 which serves to keep the pressure on the filter at about 20 psi.

A small portion of the discharge from filter 546 is fed to a pump 550 which is similar to pump 528. Pump 550 is driven by an air motor 552 which is connected to the ship's air supply through a valve 556 and a regulator and gauge 554. A by-pass valve 551 is connected across pump 550. By-pass valves 529 and 551 are used as a coarse adjustment of the flow rate.

The output from pump 550 now flows in a tube 542 of economizer heat exchanger 558. Valve 560 has the same calibrating function as valve 94 of FIG. 1. The streams in tubes 540 and 542 flow at about 0.15 gallons per minute (gpm). The flow is regulated by a flow regulator in each stream which are designated 562 and 564. The discharge from the two flow regulators enter a pair of tubes 566 and 568 in a heat exchanger 570. Heat exchanger 570 comprises a block of solid metal such as copper or aluminum into which the two tubes 566 and 568 in helical form surrounded by a larger surrounding outer tube 572 have been embedded. Liquid from a constant temperature bath 574 is pumped by means of a pump 576 into tube 572. Pump 576 is operated by motor 578 which is connected to the ship air supply through a valve 580 and a regulator and gauge 582.

The two streams emerging from tubes 568 and 566 are fed respectively to transducer assemblies 586 and 588 of differential transducer assembly 584. A solvent extraction chamber 590 is connected in the standard or reference stream before the liquid enters transducer assembly 586. It contains carbon tetrachloride or a similar solvent which will absorb the dissolved and residual suspended hydrocarbons which are contained in the reference liquid. Some of the solvent may dissolve into the water but this will not be objectionable as long as the amount remains constant. The dissolved solvent will cause a zero shift but this can be corrected for or nulled out provided the shift is always the same. Solvent extraction chamber 590 is placed before the differential transducer assembly 584 because at this point it is exposed to relatively constant temperatures and pressures. As a result, the amount of dissolved solvent will be constant.

The liquids flow through the transducer assemblies 586 and 588 to flowmeters 592 and 594. A cross connect valve 600 is closed and the flowmeters are used to adjust the flows in each stream by means of the flow regulators 562 and 564. In this way, each flowmeter is only affected by the flow in its stream. The flows in the streams are adjusted so that they are approximately equal by means of the flow regulators. Once the flows are equalized, valve 600, which is located as closely as possible to the transducer assemblies is opened. This cross connect assures that the transducers are always at the same pressure although there may be fluctuations in the absolute pressure. These fluctuations will cause changes in the absolute sound velocity in both streams but they will be of no consequence as long as both streams fluctuate the same amount. It is important that there be no differential pressure between the two streams as any such difference will introduce an error in the differential sound velocity and an attendant concentration measurement error.

The two streams combine at the discharge from the flowmeters and are fed back onto economizer heat exchanger 538. There, they dump their latent heat back into the incoming liquid. The combined streams then exit from the economizer 538 through a back pressure regulator 596 and a check valve 598 to the overflow or slop tank. Back pressure regulator 596 is set at approximately 60 – 80 psi to maintain pressure on the line so that dissolved gases do not flash into bubbles which would cause sound velocity measurement errors.

A temperature sensor 602 is associated with transducer assembly 586 and a temperature sensor 604 is associated with transducer assembly 588. Similarly, a transducer 606 is mounted in assembly 586 and a transducer 608 is mounted in assembly 588. The signals from the reference transducer 606 have been designated as A and those from unknown transducer 608 as B.

The outputs from transducers 606 and 608 are fed to differential sound velocity circuits 610 and then to frequency difference and zeroing circuits 612. The output of circuits 612 is fed to a temperature compensation circuit 614 and then to a signal conditioning circuit 616 whose output is fed to the desired displays and/or shut-off controls.

Figure 4A:
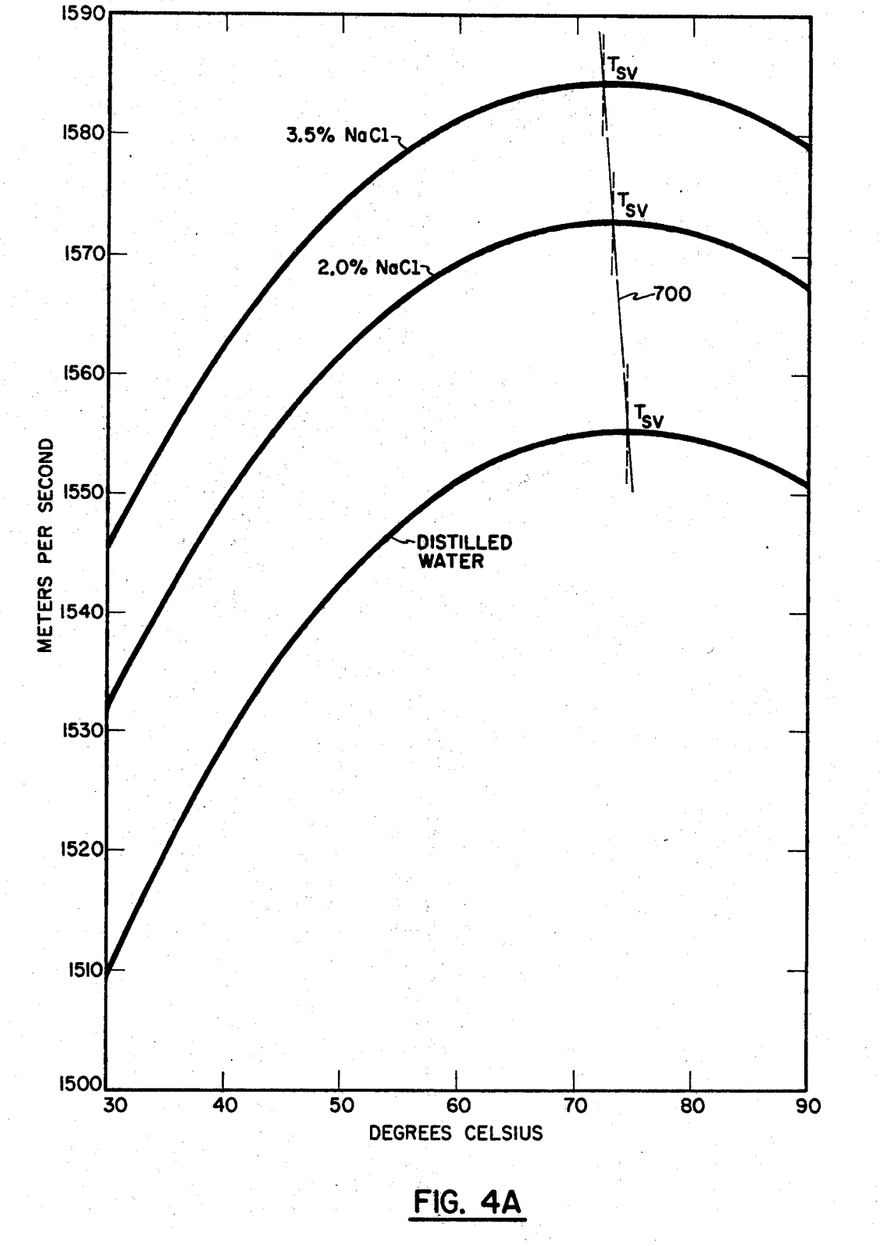
FIG. 4A is a plot on an enlarged scale, similar to that of FIG. 4, of sound velocity against temperature for different concentrations of salt in water.
Figure 4B:
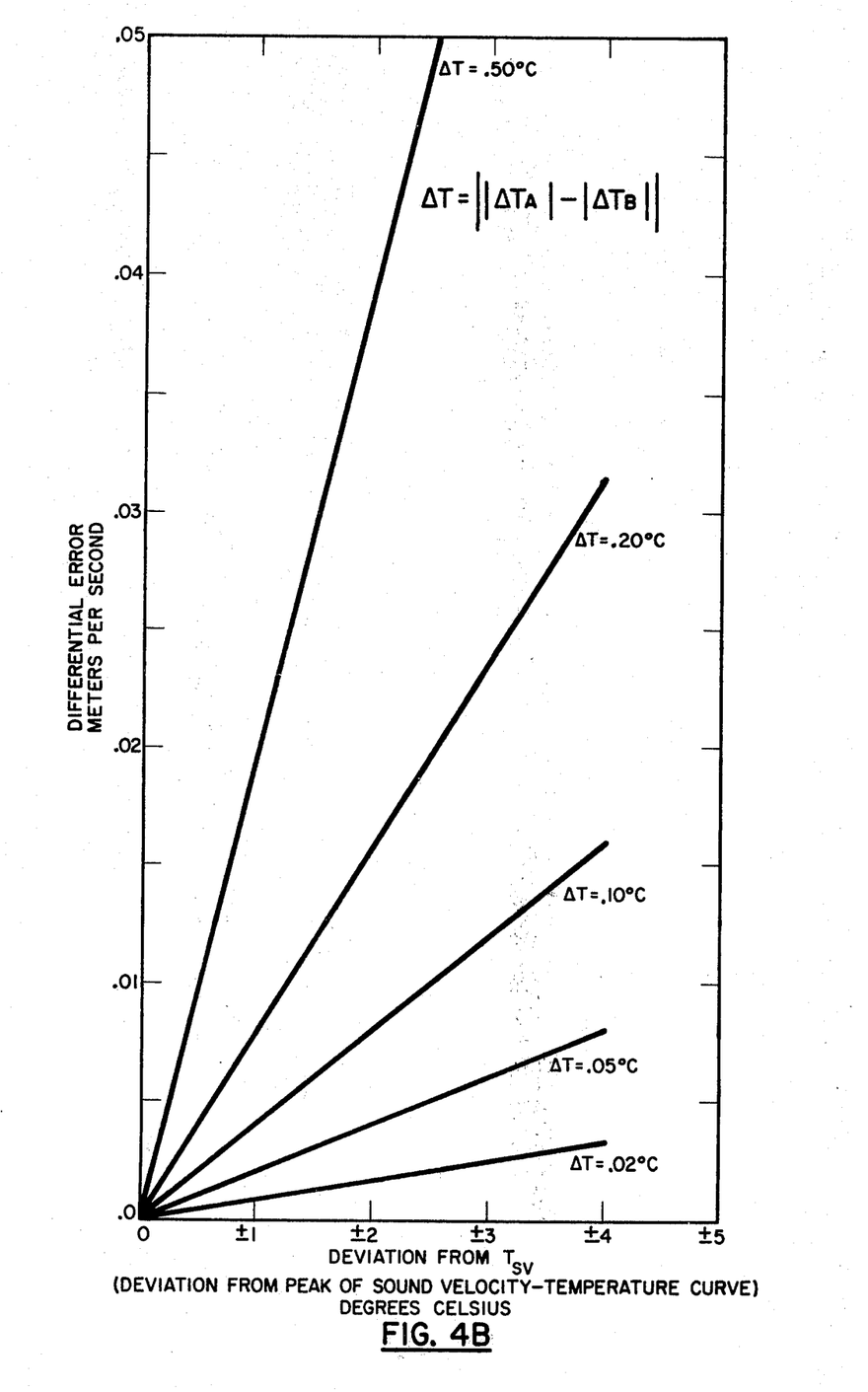
FIG. 4B is a plot of a family of curves for various cell temperature differences of the change in sound velocity and oil pollution against temperature deviation.

Turning to FIG. 4A, which is a plot of sound velocity against temperature for distilled water and for water of two different values of salinity, it can be seen that each of them has a peak temperature, designated $T_{SV}$. This point is defined mathematically as $$\frac{d[C(T)]}{dT} = 0$$

and $T = T_{SV}$; where $C(T)$ is a function describing the sound velocity — temperature relationship for a given salinity of water. Intercept line 700 connects the $T_{SV}$ peaks of the curves.

Temperature sensors 602 and 604 are connected to temperature sensor circuits 618 (FIG. 1A). The temperature of the fluid in transducer assembly A, designated $T_A$, is obtained from the temperature sensor 602 and temperature sensor circuits 618 and that in transducer assembly B, designated $T_B$, is obtained from temperature sensor 604 and temperature sensor circuits 618.

The errors caused by temperature differences in the two transducer assemblies are a function of the difference between the temperatures of the two transducer assemblies and the deviation of these temperatures from the desired $T_{SV}$ for the particular water salinity. The error $\Sigma$ is expressed as follows: $\Sigma = \Sigma (T_A, T_B, T_{SV})$ If $\Delta T_A = T_A - T_{SV}$ and $\Delta T_B = T_B - T_{SV}$, then $\Sigma = \Sigma (\Delta T_A, \Delta T_B)$.

From the above equation it can be seen that three parameters must be known in order to correct temperature errors, namely $T_A$, $T_B$ and $T_{SV}$. $T_A$ and $T_B$ are obtained in the manner described above and $T_{SV}$ is obtained from $f_A$, at the output of differential sound velocity circuits 610 and frequency to voltage converter 620. $\Delta T_A$ and $\Delta T_B$ are obtained by the operation of the output of frequency to voltage converter 620 on the temperature sensor circuits 618.

The $\Delta T_A$ output of temperature sensor circuits 618 is fed to temperature control circuit 622 which in turn controls the operation of a heater 624 which in turn maintains the temperature of the constant temperature bath 574.

The outputs of temperature sensor circuits 618 are also fed to a ready indicator 626 such as a lamp which lights when a predetermined temperature is reached. The signals $\Delta T_A$, $\Delta T_B$ and the output of frequency difference and zeroing circuits 612 are fed to temperature compensation circuits 614. In circuits 614 the above signals are combined so as to compensate for errors caused by temperature differences in the two transducer assemblies. The output of circuits 614 is fed to a signal conditioning circuit 616 which converts the signal to be usable in one or more displays and/or to operate shut-off controls.

Figure 5:
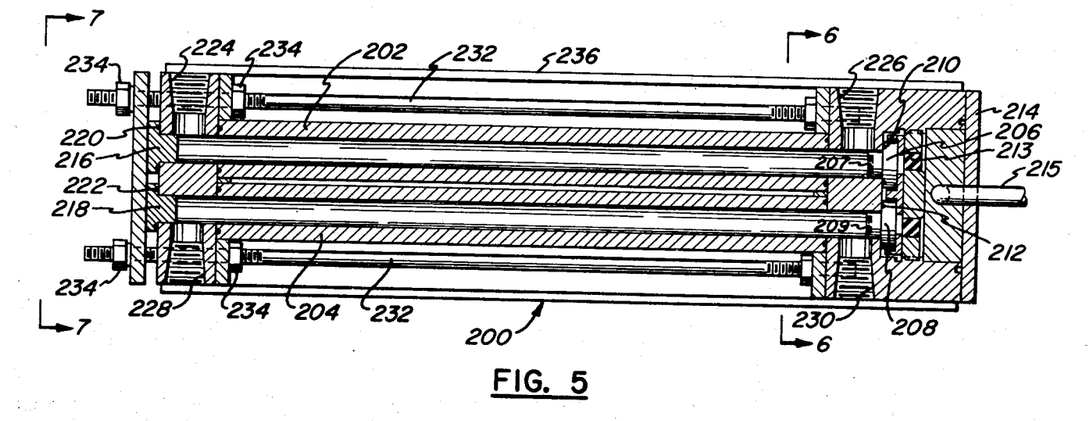
FIG. 5 is an elevational view, partly in section, of a differential transducer assembly used in the system of the invention.
Figure 6:
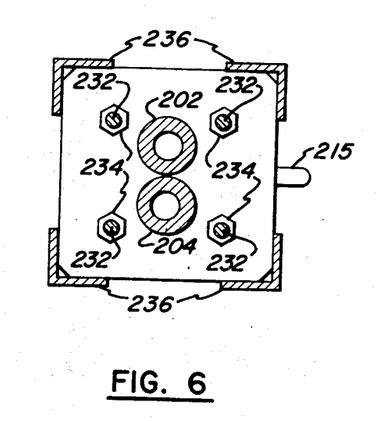
FIG. 6 is a sectional view taken on lines 6—6 of FIG. 5, viewed in the direction of the arrows.
Figure 7:
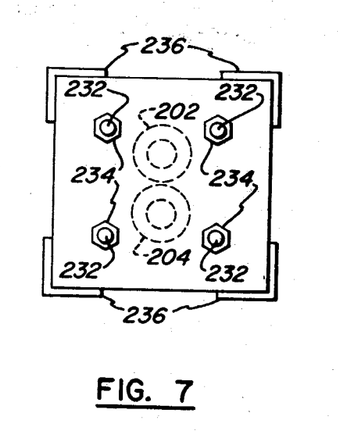
FIG. 7 is a view in the direction of arrows 7—7 of FIG. 5.

FIGS. 5–7 illustrate a differential transducer assembly 200 which may be used with the system of the invention. It is seen to comprise a pair of side by side cylindrical housings 202 and 204. Preferably, these housings are cut from the same piece of stock so that their thermal coefficients of expansion are essentially the same.

A transducer housing 206 containing a disk shaped ceramic transducer 207 is mounted in one end of housing 202 and a similar transducer housing 208 containing a similar transducer 209 is mounted in one end of housing 204. The housings 206 and 208 are sealed by O-rings 210 and 212, respectively, and are held in place by a threaded washer 213. The electrical leads are brought out through conduit 215.

A reflector housing 216 is mounted opposite transducer housing 206 and a reflector housing 218 is mounted opposite transducer housing 208. They are sealed by O-rings 220 and 222, respectively.

Solution enters housing 202 through nipple fitting 224, flows through housing 202 and exits through nipple fitting 226. This flow may be reversed, if desired. However, it is important to good operation that the faces of the transducer housing and the reflector be subjected to the flow. Similar nipple fittings 228 and 230 are provided for housing 204.

The entire assembly or housing 200 is held in position by threaded rods 232, nuts 234 and angle irons 236 so that the relationship between housings 202 and 204 remains constant mechanically.

Figure 8:
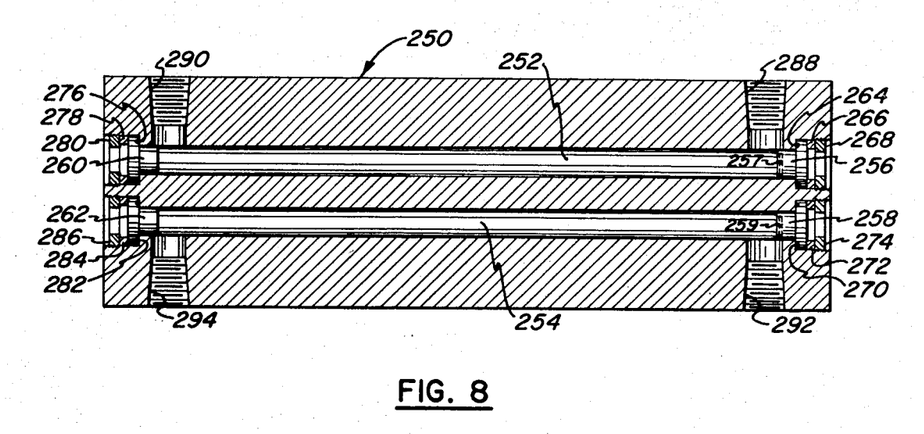
FIG. 8 is a view, similar to that of FIG. 5 of another differential transducer assembly used in the system of the invention.

FIG. 8 illustrates a further embodiment of a differential transducer assembly 250 to be used with the system of FIG. 1. Assembly 250 is formed from a single piece of material and two identical, parallel bores 252 and 254 are drilled in the piece. A transducer assembly 256 containing a transducer 257 is mounted in one end of bore 252 and a similar transducer assembly 258 containing a transducer 259 is mounted in one end of bore 254. A reflector assembly 260 is mounted opposite transducer assembly 256 and a similar reflector assembly 262 is mounted opposite transducer assembly 258.

Transducer assembly 256 is sealed by an O-ring 264 and is held in place by washer 266 and nut 268. Transducer assembly 258 is sealed by an O-ring 270 and is held in place by washer 272 and nut 274. Reflector assembly 260 is sealed by O-ring 276 and is held in place by washer 278 and nut 280 and reflector assembly 262 is sealed by O-ring 282 and is held in place by washer 284 and nut 286. Nipple fittings 288 and 290 are provided to permit liquid flow through bore 252 and nipple fittings 292 and 294 perform the same function in connection with bore 254.

Figure 9:
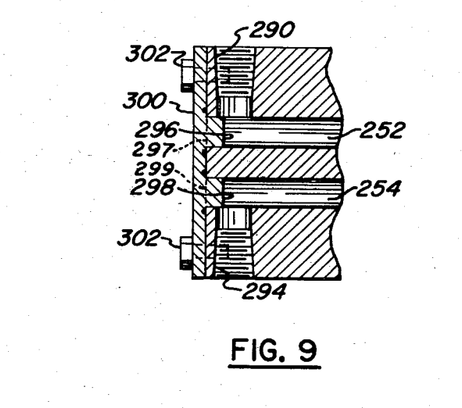
FIG. 9 is a view, similar to that of FIG. 8 of an alternate embodiment of the reflector end of the differential transducer assembly of FIG. 8.

In FIG. 9, there is shown an alternate embodiment of the reflector end of differential transducer assembly 250. The reflector elements 296 and 298 are affixed to a single piece of stock 300 along lines 297 and 299, respectively. Piece 300 is held in place by bolts 302. If possible, it is desirable to machine the reflectors as unitary parts of piece 300.

Figure 10:
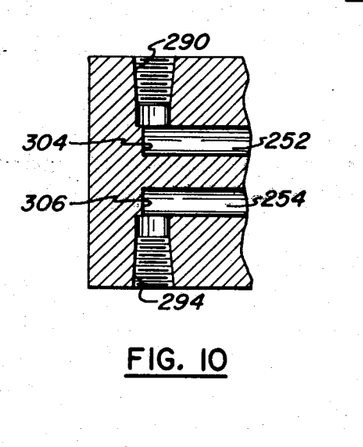
FIG. 10 is a view, similar to that of FIG. 9 of a further alternate embodiment of the reflector end of the differential transducer assembly of FIG. 8.

In FIG. 10 there is shown a still further embodiment of the reflector end of differential transducer assembly 250. The bores 252 and 254 stop before going through the end. They are accurately bored to the same length so the reflector faces 304 and 306 will be contacted by the fluid flow in the bores.

While particular embodiments of the apparatus of the invention have been shown and described, it is apparent to those skilled in the art that modifications are possible without departing from the spirit of the invention and the scope of the subjoined claims.

The embodiments of the invention in which an exclusive property or privilege is claimed are defined as follows:

1. In a system for measuring the concentration of hydrocarbons in water while the liquid is flowing from a source thereof, the improvement comprising:
  means for selecting a continuous sample of the flowing liquid;
  separator means for separating the hydrocarbons from the water to deliver a standard solution at its output;
  means for diverting a portion of the same sample to the separator means;
  a differential transducer assembly having a first transducer assembly having a first electroacoustic transducer and a first housing, and a second transducer assembly having a second electroacoustic transducer and a second housing;
  first connecting means connecting the standard solution output of the separator to the first housing;
  second connecting means connecting the second housing to the source of the sample (unknown);
  pressure equalizing means connected to the output of the first housing and the output of the second housing;
  a discharge line connected after the pressure equalizing means such that the standard solution flows through the first housing to the discharge line and the unknown solution flows through the second housing to the discharge line;
  excitation means for exciting the first transducer and the second transducer to thereby produce an acoustic wave in each of the housings;
  difference measuring means for measuring the difference between the sound velocity in the second housing and that in the first housing which difference is a function of the concentration of hydrocarbons in the unknown.

2. The invention of claim 1 wherein the excitation means comprises:
  a first oscillator associated with the first transducer;
  a second oscillator associated with the second transducer; and
  means for alternately exciting the transducers.

3. The invention of claim 2 wherein:
  the first transducer assembly and the second transducer assembly are side by side and have substantially identical dimensions and thermal characteristics.

4. The invention of claim 2 including:
  means for maintaining the temperature of the standard solution and the unknown in their respective housings substantially the same.

5. The invention of claim 4 wherein:
  the first transducer assembly and the second transducer assembly are side by side and have substantially identical dimensions and thermal characteristics.

6. The invention of claim 4 including:
  a first reflector mounted in the first housing such that the acoustic wave transmitted through the standard solution is returned to the first transducer; and
  a second reflector mounted in the second housing such that the acoustic wave transmitted through the unknown is returned to the second transducer.

7. The invention of claim 6 wherein:
  the first transducer assembly and the second transducer assembly are side by side and have substantially identical dimensions and thermal characteristics.

8. The invention of claim 6 wherein the difference measuring means comprises:
  amplitude servo means connected to the transducers such that the amplitude of the signal received by each of them is maintained constant;
  frequency servo means having its input connected to the transducer and its output connected to the oscillator associated therewith such that the frequency of said oscillator is maintained within predetermined limits; and
  means for obtaining the difference between the frequencies of the two oscillators.

9. The invention of claim 8 including:
  means for converting the difference between the frequencies into an analog display.

10. The invention of claim 9 wherein:
  the first transducer assembly and the second transducer assembly are side by side and have substantially identical dimensions and thermal characteristics.

11. The invention of claim 8 including:
  means for actuating an alarm when the difference between the frequencies exceeds a predetermined value.

12. The invention of claim 11 wherein:
  the first transducer assembly and the second transducer assembly are side by side and have substantially identical dimensions and thermal characteristics.

13. The invention of claim 8 including:
  means for shutting down the system when the difference between the frequencies exceeds a predetermined value.

14. The invention of claim 13 wherein:
  the first transducer assembly and the second transducer assembly are side by side and have substantially identical dimensions and thermal characteristics.

15. The invention of claim 8 including:
  means for converting the difference between the frequencies into a digital signal.

16. The invention of claim 15 wherein:
  the first transducer assembly and the second transducer assembly are side by side and have substantially identical dimensions and thermal characteristics.

17. The invention of claim 8 including calibration means comprising:
means for determining which of the two sound paths operates at the higher frequency with a standard solution in both housings; and
means for adjusting the output of the frequency servo means associated with the sound paths having the higher frequency to obtain the same frequency over both sound paths.

18. The invention of claim 17 wherein:
the first transducer assembly and the second transducer assembly are side by side and have substantially identical dimensions and thermal characteristics.

19. The invention of claim 8 wherein:
the first transducer assembly and the second transducer assembly are side by side and have substantially identical dimensions and thermal characteristics.

20. The invention of claim 1 wherein:
the first transducer assembly and the second transducer assembly are side by side and have substantially identical dimensions and thermal characteristics.

21. The invention of claim 1 wherein:
the pressure equalizing means comprises a valve connected between the output of the first housing and the output of the second housing.

22. The invention of claim 21 wherein:
the first transducer assembly and the second transducer assembly are side by side and have substantially identical dimensions and thermal characteristics.

23. The invention of claim 21 wherein the excitation means comprises:
a first oscillator associated with the first transducer;
a second oscillator associated with the second transducer; and
means for alternately exciting the transducers.

24. The invention of claim 23 wherein:
the first transducer assembly and the second transducer assembly are side by side and have substantially identical dimensions and thermal characteristics.

25. The invention of claim 23 including:
means for maintaining the temperature of the standard solution and the unknown in their respective housings substantially the same.

26. The invention of claim 25 wherein:
the first transducer assembly and the second transducer assembly are side by side and have substantially identical dimensions and thermal characteristics.

27. The invention of claim 25 including:
a first reflector mounted in the first housing such that the acoustic wave transmitted through the standard solution is returned to the first transducer; and
a second reflector mounted in the second housing such that the acoustic wave transmitted through the unknown is returned to the second transducer.

28. The invention of claim 27 wherein:
the first transducer assembly and the second transducer assembly are side by side and have substantially identical dimensions and thermal characteristics.

29. The invention of claim 27 wherein the difference measuring means comprises:
amplitude servo means connected to the transducers such that the amplitude of the signal received by each of them is maintained constant;
frequency servo means having its input connected to the transducer and its output connected to the oscillator associated therewith such that the frequency of said oscillator is maintained within predetermined limits; and
means of obtaining the difference between the freqencies of the two oscillators.

30. The invention of claim 29 including:
means for converting the difference between the frequencies into an analog display.

31. The invention of claim 30 wherein:
the first transducer assembly and the second transducer assembly are side by side and have substantially identical dimensions and thermal characteristics.

32. The invention of claim 29 including:
means for actuating an alarm when the difference between the frequencies exceeds a predetermined value.

33. The invention of claim 32 wherein:
the first transducer assembly and the second transducer assembly are side by side and have substantially identical dimensions and thermal characteristics.

34. The invention of claim 29 including:
means for shutting down the system when the difference between the frequencies exceeds a predetermined value.

35. The invention of claim 34 wherein:
the first transducer assembly and the second transducer assembly are side by side and have substantially identical dimensions and thermal characteristics.

36. The invention of claim 29 including:
means for converting the difference between the frequencies into a digital signal.

37. The invention of claim 36 wherein:
the first transducer assembly and the second transducer assembly are side by side and have substantially identical dimensions and thermal characteristics.

38. The invention of claim 29 including calibration means comprising:
means for determining which of the two sound paths operates at the higher frequency with a standard solution in both housings; and
means for adjusting the output of the frequency servo means associated with the sound paths having the higher frequency to obtain the same frequency over both sound paths.

39. The invention of claim 38 wherein:
the first transducer assembly and the second transducer assembly are side by side and have substantially identical dimensions and thermal characteristics.

40. The invention of claim 29 wherein:
the first transducer assembly and the second transducer assembly are side by side and have substantially identical dimensions and thermal characteristics.

41. The invention of claim 21 including temperature correcting means for applying a temperature correction signal to the measurement of the difference between the sound velocity in the second housing and the sound velocity in the first housing to thereby minimize any error in the measurement of the concentration of hydrocarbons in the unknown.

42. The invention of claim 41 wherein:
the first transducer assembly and the second transducer assembly are side by side and have substantially indentical dimensions and thermal characteristics.

43. The invention of claim 41 wherein the excitation means comprises:
a first oscillator associated with the first transducer;
a second oscillator associated with the second transducer; and
means for alternately exciting the transducers.

44. The invention of claim 43 wherein:
the first transducer assembly and the second transducer assembly are side by side and have substantially identical dimensions and thermal characteristics.

45. The invention of claim 43 including:
means for maintaining the temperature of the standard solution and the unknown in their respective housings substantially the same.

46. The invention of claim 45 wherein:
the first transducer assembly and the second transducer assembly are side by side and have substantially identical dimensions and thermal characteristics.

47. The invention of claim 45 including:
a first reflector mounted in the first housing such that the acoustic wave transmitted through the standard solution is returned to the first transducer; and
a second reflector mounted in the second housing such that the acoustic wave transmitted through the unknown is returned to the second transducer.

48. The invention of claim 47 wherein the difference measuring means comprises:
amplitude servo means connected to the transducers such that the amplitude of the signal received by each of them is maintained constant;
frequency servo means having its input connected to the transducer and its output connected to the oscillator associated therewith such that the frequency of said oscillator is maintained within predetermined limits; and
means for obtaining the difference between the frequencies of the two oscillators.

49. The invention of claim 48 including:
means for converting the difference between the frequencies into an analog display.

50. The invention of claim 49 wherein:
the first transducer assembly and the second transducer assembly are side by side and have substantially identical dimensions and thermal characteristics.

51. The invention of claim 48 including:
means for actuating an alarm when the difference between the frequencies exceeds a predetermined value.

52. The invention of claim 51 wherein:
the first transducer assembly and the second transducer assembly are side by side and have substantially identical dimensions and thermal characteristics.

53. The invention of claim 48 including:
means for shutting down the system when the difference between the frequencies exceeds a predetermined value.

54. The invention of claim 53 wherein:
the first transducer assembly and the second transducer assembly are side by side and have substantially identical dimensions and thermal characteristics.

55. The invention of claim 48 including:
means for converting the difference between the frequencies into a digital signal.

56. The invention of claim 55 wherein:
the first transducer assembly and the second transducer assembly are side by side and have substantially identical dimensions and thermal characteristics.

57. The invention of claim 48 including calibration means comprising:
means for determining which of the two sound paths operates at the higher frequency with a standard solution in both housings; and
means for adjusting the output of the frequency servo means associated with the sound paths having the higher frequency to obtain the same frequency over both sound paths.

58. The invention of claim 57 wherein:
the first transducer assembly and the second transducer assembly are side by side and have substantially identical dimensions and thermal characteristics.

59. The invention of claim 48 wherein:
the first transducer assembly and the second transducer assembly are side by side and have substantially identical dimensions and thermal characteristics.

60. The invention of claim 47 wherein:
the first transducer assembly and the second transducer assembly are side by side and have substantially identical dimensions and thermal characteristics.

* * * * *